United States Patent
Plos

(10) Patent No.: US 6,733,539 B2
(45) Date of Patent: May 11, 2004

(54) COMPOSITIONS FOR THE OXIDATION DYEING OF KERATINOUS FIBERS COMPRISING AT LEAST ONE OXIDATION DYE AND AT LEAST ONE ENZYMATIC OXIDIZING AGENT, AND DYEING METHODS

(75) Inventor: Grégory Plos, Paris (FR)

(73) Assignee: L'Oreal S.A., Paris (FR)

(*) Notice: Subject to any disclaimer, the term of this patent is extended or adjusted under 35 U.S.C. 154(b) by 0 days.

(21) Appl. No.: 09/820,016

(22) Filed: Mar. 29, 2001

(65) Prior Publication Data

US 2002/0170122 A9 Nov. 21, 2002

(30) Foreign Application Priority Data

Mar. 30, 2000 (FR) .............................. 00 04061

(51) Int. Cl.$^7$ ................................. A61K 7/13
(52) U.S. Cl. ................. 8/405; 8/406; 8/407; 8/409; 8/410; 8/421; 8/435; 8/568
(58) Field of Search .................. 8/405, 406, 407, 8/409, 410, 421, 435, 568

(56) References Cited

U.S. PATENT DOCUMENTS

| | | | |
|---|---|---|---|
| 4,003,699 A | 1/1977 | Rose et al. | 8/10.2 |
| 4,473,375 A | 9/1984 | Clausen | 8/409 |
| 4,784,667 A | 11/1988 | Maak et al. | 8/409 |
| 4,823,985 A | 4/1989 | Grollier et al. | 222/1 |
| 5,061,289 A | 10/1991 | Clausen et al. | 8/405 |
| 5,380,340 A | 1/1995 | Neunhoeffer et al. | 8/409 |
| 5,766,576 A | 6/1998 | Löwe et al. | 424/62 |
| 5,948,121 A | 9/1999 | Aaslyng et al. | 8/401 |
| 6,001,134 A | 12/1999 | Sorensen | 8/401 |
| 6,099,592 A | 8/2000 | Vidal et al. | 8/409 |
| 6,203,579 B1 * | 3/2001 | Moeller et al. | 8/409 |
| 6,309,426 B1 * | 10/2001 | Dias et al. | 8/406 |
| 6,312,477 B1 * | 11/2001 | De La Mettrie et al. | 424/70.11 |

FOREIGN PATENT DOCUMENTS

| | | | |
|---|---|---|---|
| DE | 23 59 399 | 6/1975 | |
| DE | 31 32 885 | 3/1983 | |
| DE | 38 43 892 | 6/1990 | |
| DE | 41 33 957 | 4/1993 | |
| DE | 195 43 988 | 5/1997 | |
| DE | 198 47 276 | 4/2000 | |
| EP | 0 106 987 | 5/1984 | |
| EP | 0 310 675 | 4/1989 | |
| EP | 0 504 005 | 9/1992 | |
| FR | 2 112 549 | 6/1972 | |
| FR | 2 586 913 | 3/1987 | |
| FR | 2 694 018 | 1/1994 | |
| FR | 2 733 749 | 11/1996 | |
| FR | 2 750 048 | 12/1997 | |
| FR | 2 763 841 | 12/1998 | |
| FR | 2 769 214 | 4/1999 | |
| FR | 2 776 186 | 9/1999 | |
| GB | 1 026 978 | 4/1966 | |
| GB | 1 153 196 | 5/1969 | |
| JP | 2-19576 | 1/1990 | |
| JP | 9-110659 | 4/1997 | |
| WO | WO 94/08969 | 4/1994 | |
| WO | WO 94/08970 | 4/1994 | |
| WO | WO 95/07988 | 3/1995 | |
| WO | WO 95/33836 | 12/1995 | |
| WO | WO 95/33837 | 12/1995 | |
| WO | WO 96/00290 | 1/1996 | |
| WO | WO 96/15765 | 5/1996 | |
| WO | WO 97/19998 | 6/1997 | |
| WO | WO 97/19999 | 6/1997 | |
| WO | WO009840471 | * 9/1998 | ............ C12N/9/96 |

OTHER PUBLICATIONS

English language Derwent Abstract of DE 198 47 276, Apr. 20, 2000.
English language Derwent Abstract of EP 0 504 005, Sep. 16, 1992.
English language Derwent Abstract of FR 2 112 549, Jun. 16, 1972.
English language Derwent Abstract of FR 2 694 018, Jan. 28, 1994.
English language Derwent Abstract of FR 2 750 048, Dec. 26, 1997.
English language Derwent Abstract of FR 2 763 841, Dec. 4, 1998.
English language Derwent Abstract of FR 2 769 214, Apr. 9, 1999.
English language Derwent Abstract of FR 2 776 186, Sep. 24, 1999.
English language Derwent Abstract of JP 2–19576, Jan. 23, 1990.
English language Derwent Abstract of JP 9–110659, Apr. 28, 1997.

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner, L.L.P.

(57) ABSTRACT

Compositions for oxidation dyeing of keratinous fibers, for example, human keratinous fibers such as hair, comprising, in a medium suitable for dyeing, at least one enzymatic oxidizing agent and at least one oxidation dye chosen from the pyridine compounds and acid addition salts, of formula (I) and processes comprising such compositions.

86 Claims, No Drawings

COMPOSITIONS FOR THE OXIDATION DYEING OF KERATINOUS FIBERS COMPRISING AT LEAST ONE OXIDATION DYE AND AT LEAST ONE ENZYMATIC OXIDIZING AGENT, AND DYEING METHODS

The invention relates to a ready-to-use composition for the oxidation dyeing of keratinous fibers, such as, human keratinous fibers, for example, hair, comprising, in a medium which is suitable for dyeing, at least one oxidation dye chosen from pyridines of formula (I), and at least one enzymatic oxidizing agent, and the oxidation dyeing method for using them.

It is known to dye keratinous fibers, for example, human hair, with dye compositions containing oxidation dye precursors, such as, ortho- or para-phenylenediamines, ortho- or para-aminophenols and heterocyclic bases, which are generally referred to as oxidation bases. Oxidation dye precursors, or oxidation bases, are colorless or weakly colored compounds which, when combined with oxidizing products, can give rise to colored compounds and dyes by an oxidative condensation process.

It is also known that it is possible to vary the shades obtained with these oxidation bases by combining them with couplers or color modifiers, the latter chosen, for example, from aromatic meta-diamines, meta-aminophenols, meta-diphenols and certain heterocyclic compounds such as, indoles, indolines and pyridine derivatives (see, for example, patent applications DE 3 132 885 and EP-A-0 106 987).

The variety of molecules used as oxidation bases and couplers allows a wide rich palette of colors to be obtained.

The "permanent" colors obtained using these oxidation dyes may moreover satisfy at least one of a number of objectives. Thus, it should, for example, satisfy at least one of the following: be without toxicological drawbacks, make it possible to obtain shades in the desired intensity, and exhibit good resistance towards external agents (at least one of light, adverse weather conditions, washing, permanent waving, perspiration, and rubbing).

The dyes may also cover white and gray hair and, may also be the least selective possible, that is to say, make it possible to obtain the smallest possible differences in color right along the same keratinous fiber, which may indeed be differently sensitised (i.e. damaged) between its tip and its root.

Oxidation dyeing of keratinous fibers is generally carried out in alkaline medium, in the presence of hydrogen peroxide. However, the use of alkaline media in the presence of hydrogen peroxide may possess the undesirable drawbacks of causing appreciable degradation of the fibers, as well as, considerable bleaching of the keratinous fibers.

Oxidation dyeing of keratinous fibers may also be carried out using oxidizing systems other than hydrogen peroxide, for example, enzymatic systems. Patent application EP-A-0,310,675, has proposed dyeing keratinous fibers with compositions comprising an oxidation base and optionally a coupler, in combination with enzymes, such as, pyranose oxidase, glucose oxidase and uricase, in the presence of a donor for the said enzymes. Although these compounds are used under conditions which may diminish the degradation of the keratinous fibers below the level of degradation found by the dyes used in the presence of hydrogen peroxide, these dyeing processes nevertheless lead to colors which are not entirely satisfactory. For example, the processes may affect the intensity (strength) of the colors or the colors' resistance to the various attacking factors to which the hair may be subjected.

The inventor has now discovered that combination of at least one oxidation dye chosen from the pyridines of formula (I), defined below, and at least one enzymatic oxidizing agent make it possible to obtain dye compositions leading to at least one of the following advantages: intense colors without giving rise to any significant degradation of the keratinous fibers, colors which are not very selective, and properties of resistance to the various treatments to which keratinous fibers, such as, hair may be subjected.

One embodiment of the invention is thus a ready-to-use composition for the oxidation dyeing of keratinous fibers, and in particular human keratinous fibers, for example, hair, comprising, in a medium suitable for dyeing:

(a) at least one oxidation dye chosen from the pyridines of formula (I), and acid addition salts thereof:

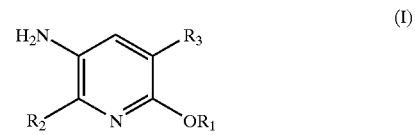

wherein:
 $R_1$ is chosen from a $(C_1-C_4)$alkyl group, a $(C_1-C_4)$ monohydroxyalkyl group, and a $(C_2-C_4)$ polyhydroxyalkyl group,
 $R_2$ is chosen from a $(C_1-C_4)$alkoxy group, a $(C_1-C_4)$ monohydroxyalkoxy group, a $(C_2-C_4)$ polyhydroxyalkoxy group, an amino group, a mono $(C_1-C_4)$alkylamino group, a di-$(C_1-C_4)$alkylamino group, a monophenylamino group, a monohydroxyphenylamino group, a monoalkoxyphenylamino group, a monohydroxy$(C_1-C_4)$alkylamino group, a dihydroxy-$(C_1-C_4)$alkylamino group, a monohydroxy-$(C_2-C_4)$ alkylamino group, a dihydroxy-$(C_2-C_4)$alkylamino group, a $(C_1-C_4)$alkylmonohydroxy-$(C_1-C_4)$ alkylamino group and a $(C_1-C_4)$alkyl-polyhydroxy $(C_2-C_4)$alkylamino group,
 $R_3$ is chosen from a hydrogen atom, an amino group, a mono$(C_1-C_4)$alkylamino group,
 a monohydroxy$(C_1-C_4)$alkylamino group and a mono(polyhydroxy$(C_2-C_4)$alkyl)amino group;
 provided that: when $R_2$ is chosen form a $(C_1-C_4)$alkoxy group, a
 $(C_1-C_4)$monohydroxyalkoxy group and a $(C_2-C_4)$ polyhydroxyalkoxy group, then $R_3$ is a hydrogen atom; and
(b) at least one enzymatic oxidizing agent chosen from:
 (i) a system comprising at least one 2-electron oxidoreductase and its corresponding at least one donor,
 (ii) at least one 4-electron oxidoreductase, and
 (iii) at least one peroxidase.

As indicated above, the colors obtained with the oxidation dyeing composition comprising a pyridine of formula (I) according to the invention, can be intense and can contribute to a palette of highly chromatic colors. Such compositions may also exhibit properties of resistance towards the action of various external agents (at least one of light, adverse weather conditions, washing, permanent waving and perspiration).

One embodiment of the invention is a method for the oxidation dyeing of keratinous fibers using the ready-to-use dye composition described above.

In one embodiment of the invention, the at least one oxidation dye of formula (I) is chosen from 2,6-dimethoxy-3,5-diaminopyridine, 2,3-diamino-6-methoxypyridine, 2-methylamino-3-amino-6-methoxypyridine, 2-(2'-hydroxyphenyl)amino-3-amino-6-methoxypyridine, 2-(4'-hydroxyphenyl)amino-3-amino-6-methoxypyridine, 2-(4'-methoxyphenyl)amino-3-amino-6-methoxypyridine, 2-phenylamino-3-amino-6-methoxypyridine, and acid addition salts thereof.

In another embodiment, the at least one oxidation dye of formula (I) is chosen from 2,6-dimethoxy-3,5-diaminopyridine and optionally, at least one acid addition salt thereof.

The at least one oxidation dye of formula (I) according to the invention, may be present, for example, in an amount ranging from 0.0001 to 10% by weight relative to the total weight of the dye composition. In another embodiment of the invention, the at least one oxidation dye of formula (I) is present in an amount ranging from 0.005 to 5% by weight relative to the total weight of the dye composition.

In addition to the at least one oxidation dye of formula (I) above, the ready-to-use dye composition of the invention may optionally contain at least one oxidation base and at least one coupler.

According to one embodiment, the ready-to-use dye composition further comprises at least one oxidation base.

The nature of the at least one oxidation base used in the ready-to-use dye composition is not critical. The at least one oxidation base, for example, may be chosen from para-phenylenediamines, double bases, para-aminophenols, ortho-aminophenols and heterocyclic oxidation bases. Examples of the para-phenylenediamines which can be used as oxidation bases in the dye compositions in accordance with the invention, may be chosen from the compounds of formula (II) and acid addition salts thereof:

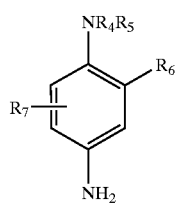

(II)

wherein:
- $R_4$ is chosen from a hydrogen atom, a $(C_1-C_4)$alkyl group optionally substituted with a nitrogenous group, a $(C_1-C_4)$monohydroxyalkyl group, a $(C_2-C_4)$ polyhydroxyalkyl group, a $(C_1-C_4)$alkoxy$(C_1-C_4)$ alkyl group, a phenyl group and a 4'-aminophenyl group;
- $R_5$ is chosen from a hydrogen atom, a $C_1-C_4$ alkyl group optionally substituted with a nitrogenous group, a $C_1-C_4$ monohydroxyalkyl group, a $C_2-C_4$ polyhydroxyalkyl group, and a $(C_1-C_4)$alkoxy$(C_1-C_4)$alkyl group;
- $R_6$ is chosen from a hydrogen atom, a halogen atom, a $(C_1-C_4)$alkyl group, a $(C_1-C_4)$monohydroxyalkyl group, a $(C_1-C_4)$hydroxyalkoxy group, an acetylamino $(C_1-C_4)$-alkoxy group, a $(C_1-C_4)$mesylaminoalkoxy group and a carbamoylamino$(C_1-C_4)$alkoxy group,
- $R_7$ is chosen from a hydrogen atom, a halogen atom and a $C_1-C_4$ alkyl group.

Examples of the above mentioned nitrogenous groups, are chosen from amino, mono$(C_1-C_4)$alkylamino, di$(C_1-C_4)$ alkylamino, tri$(C_1-C_4)$-alkylamino, monohydroxy$(C_1-C_4)$ alkylamino, imidazolinium and ammonium groups.

In one embodiment of the invention, examples of para-phenylenediamines of formula (II) above, are chosen from para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and addition salts thereof.

In another embodiment of the invention, the para-phenylenediamines of formula (II) above, are chosen from para-phenylenediamine, para-toluylenediamine, 2-isopropyl-para-phenylenediamine, 2-β-hydroxyethyl-para-phenylenediamine, 2-β-hydroxy-ethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine and acid addition salts thereof.

According to the invention, the term double bases refers to the compounds containing at least two aromatic rings comprising at least one group chosen from amino and hydroxyl groups.

In one embodiment of the invention, the double bases which can be used as oxidation bases in the dye compositions, are chosen from compounds of formula (III) below, and acid addition salts thereof:

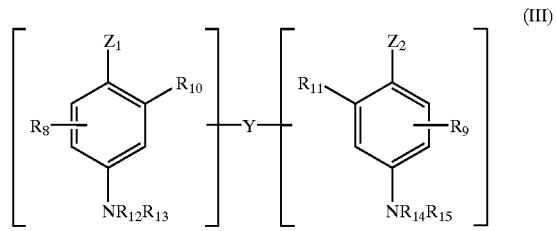

(III)

wherein:
- a linker arm Y chosen from linear and branched alkylene groups comprising from 1 to 14 carbon atoms optionally substituted with at least one group chosen from hydroxyl and $(C_1-C_6)$alkoxy groups, wherein said linear and branched alkylene groups are optionally interrupted by or terminated by at least one group chosen from nitrogenous groups and heteroatoms chosen from oxygen, sulfur, and nitrogen atoms;
- $Z_1$ and $Z_2$, which are identical or different, are each chosen from a hydroxyl group and an amino group optionally substituted with a group chosen from a $(C_1-C_4)$alkyl group and said linker arm Y;
- $R_8$ and $R_9$ which are identical or different, are each chosen from a hydrogen atom, a halogen atom, a $(C_1-C_4)$alkyl group, a ($C_1$–$C_4$)monohydroxyalkyl group, a ($C_2$–$C_4$) polyhydroxyalkyl group, a ($C_1$–$C_4$)aminoalkyl group and said linker arm Y;

$R_{10}$, $R_{11}$, $R_{12}$, $R_{13}$, $R_{14}$ and $R_{15}$, which are identical or different, are each chosen from a hydrogen atom, said linker arm Y and a ($C_1$–$C_4$)alkyl group; provided that: said compounds of formula (III) contain only one said linker arm Y per molecule.

In one embodiment of the invention, examples of the nitrogenous groups of formula (III) may be chosen from amino, mono($C_1$–$C_4$)alkylamino, di($C_1$–$C_4$)alkylamino, tri ($C_1$–$C_4$)alkylamino, monohydroxy($C_1$–$C_4$)alkylamino, imidazolinium and ammonium groups.

In one embodiment of the invention, the double bases of formula (III) are chosen from N,N'-bis(β-hydroxyethyl)-N, N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(4'-hydroxyethyl)-N,N'-bis(4-aminophenyl)-tetramethylenediamine, N,N'-bis(4-methylaminophenyl) tetramethylenediamine, N,N'-bis-(ethyl)-N,N'-bis(4'-amino-3'-methylphenyl)ethylenediamine, 1,8-bis(2,5-diaminophenoxy)-3,5-dioxaoctane, and acid addition salts thereof.

In another embodiment, the double bases of formula (III) are chosen from N,N'-bis(β-hydroxyethyl)-N,N'-bis(4'-aminophenyl)-1,3-diaminopropanol, 1,8-bis(2,5-diaminophenoxy)-3,5-dioxaoctane, and acid addition salts thereof.

In yet another embodiment, the para-aminophenols which may be used as oxidation bases in the dye compositions according to the invention, are chosen from the compounds of formula (IV), and acid addition salts thereof:

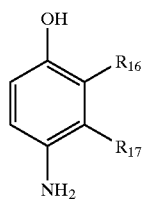

(IV)

wherein:
$R_{16}$ is chosen from a hydrogen atom, a halogen atom, a ($C_1$–$C_4$)alkyl group, a ($C_1$–$C_4$)monohydroxyalkyl group, a($C_1$–$C_4$)alkoxy($C_1$–$C_4$)alkyl group, a ($C_1$–$C_4$) aminoalkyl group and a hydroxy($C_1$–$C_4$)alkylamino ($C_1$–$C_4$)alkyl group, $R_{17}$ is chosen from a hydrogen atom, a halogen atom, a ($C_1$–$C_4$)alkyl group, ($C_1$–$C_4$)monohydroxyalkyl group, ($C_2$–$C_4$)polyhydroxyalkyl group, ($C_1$–$C_4$)aminoalkyl group, ($C_1$–$C_4$)cyanoalkyl group and a ($C_1$–$C_4$)alkoxy-($C_1$–$C_4$)alkyl group, provided that: at least one of $R_{16}$ and $R_{17}$ is a hydrogen atom.

In one embodiment of the invention, the para-aminophenols of formula (IV) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid addition salts thereof.

In another embodiment, ortho-aminophenols which can be used as oxidation bases in the dye compositions according to the invention, are chosen from 2-aminophenol, 2-amino-5-methylphenol, 2-amino-6-methylphenol, 5-acetamido-2-aminophenol, and acid addition salts thereof.

Examples of heterocyclic bases which can be used as oxidation bases in the dye compositions in according to the invention, may be chosen from pyridine derivatives, pyrimidine derivatives, pyrazolopyrimidine derivatives, pyrazole derivatives, and acid addition salts thereof.

In one embodiment, the pyridine derivatives, may include compounds described in patents GB 1,026,978 and GB 1,153,196, incorporated by reference herein, such as, 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine 3,4-diaminopyridine, and acid addition salts thereof.

In another embodiment the pyrimidine derivatives, may include compounds described in German patent DE 2,359, 399, Japanese patents JP 88-169,571 and JP 91-10659 and patent application WO 96/15765, all of which are incorporated by reference herein, such as, 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and acid addition salts thereof.

Additionally, another embodiment of the invention employs pyrazolopyrimidine derivatives disclosed in patent application FR-A-2 750 048, incorporated by reference herein, such as, pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimdine-3,7-diamine, 2,6-dimethylpyrazolo[1,5-a]pyrimidine-3,7-diamine, 2,5,N7, N7-tetramethylpyrazolo[1,5-a]pyrimidine-3,7-diamine and 3-amino-5-methyl-7-imidazolylpropylaminopyrazolo[1,5-a]pyrimidine, a corresponding tautomeric form thereof, when a tautomeric equilibrium exits, and acid addition salts thereof.

Another embodiment of the invention employs pyrazole derivatives disclosed in German patents DE 3,843,892, and DE 4,133,957 and patent applications WO 94/08969, WO 94/08970, FR—A-2,733,749 and DE 195 43 988 (all of which are incorporated by reference herein), such as, 4,5-diamino-1-methylpyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino -5-(2'-aminoethyl) amino-1,3-dimethylpyrazole, 3,4,5-triaminopyrazole, 1-methyl-3,4,5-tri-aminopyrazole, 3,5-diamino-1-methyl-4-methylaminopyrazole, 3,5-diamino -4-(1-hydroxyethyl) amino-1-methylpyrazole, and acid addition salts thereof.

According to one embodiment of the invention, the at least one oxidation base is chosen from para-phenylenediamines.

When present, the at least one oxidation base may be present in an amount ranging from 0.0005 to 12% by weight relative to the total weight of the ready-to-use dye composition. In another embodiment, the at least one oxidation base may be present in an amount ranging from 0.005 to 8% by weight relative to the total weight of the ready-to-use dye composition.

Examples of the at least one 2-electron oxidoreductase which may be used as an enzymatic oxidizing agent in the ready-to-use dye composition of the invention, may be chosen from pyranose oxidases, glucose oxidases, glycerol oxidases, lactate oxidases, pyruvate oxidases, uricases, choline oxidases, sarcosine oxidases and bilirubin oxidases.

In one embodiment, the at least one 2-electron oxidoreductase is chosen from uricases of animal, microbiological and biotechnological origin.

Examples of these uricases comprise the uricase extracted from boar's liver, the uricase from *Arthrobacter globiformis* and the uricase from *Aspergillus flavus*.

In another embodiment, the at least one 2-electron oxidoreductase may be used in pure crystalline form or in a form diluted in a diluent which is inert with respect to the at least one 2-electron oxidoreductase.

In one embodiment, the at least one 2-electron oxidoreductase in accordance with the invention, may be present in an amount ranging from 0.01 to 20% by weight relative to the total weight of the ready-to-use dye composition. In another embodiment, the at least one 2-electron oxidoreductase may be present in an amount ranging from 0.1 to 10% by weight relative to the total weight of the ready-to-use dye composition.

In yet another embodiment, the at least one enzymatic oxidizing agent is at least one 2-electron oxidoreductase and may be present in an amount ranging from 0.1 to 5% by weight relative to the total weight of the ready-to-use dye composition.

The amount of the at least one 2-electron oxidoreductase may also be defined as a function of its activity. Thus, the enzymatic activity of the at least one 2-electron oxidoreductase can be defined by the oxidation of the donor under aerobic conditions.

One unit U corresponds to the amount of the at least one 2-electron oxidoreductase which generates one $\mu$mol of hydrogen peroxide per minute at a pH of 8.5 and at a temperature of 25° C.

In one embodiment, the at least one 2-electron oxidoreductase is present in an amount ranging from 10 to $10^8$ units U per 100 g of ready-to-use dye composition.

According to the invention, the term "donor" means the various substrates participating in the functioning of the at least one 2-electron oxidoreductase.

The nature of the at least one donor (or substrate) corresponding to the enzyme varies as a function of the nature of the at least 2-electron oxidoreductase used. For example, in one embodiment, donors for the pyranose oxidases, may comprise D-glucose, L-sorbose and D-xylose; donors for the glucose oxidases may comprise D-glucose; donors for the glycerol oxidases, may comprise glycerol and dihydroxyacetone; donors for the lactate oxidases may comprise lactic acid and its salts; donors for the pyruvate oxidases may comprise pyruvic acid and its salts; donors for the uricases may comprise uric acid and its salts; donors for the choline oxidases may comprise choline and acid addition salts thereof, such as, choline hydrochloride and betaine aldehyde; donors for the sarcosine oxidases may comprise sarcosine, N-methyl-L-leucine, N-methyl-D,L-alanine and N-methyl-D,L-valine; and donors for the bilirubin oxidases may comprise bilirubin.

When utilized, the at least one donor (or substrate) is present in an amount ranging from 0.01 to 20% by weight relative to the total weight of the ready-to-use dye composition in accordance with the invention. In another embodiment, the at least one donor (or substrate) is present in an amount ranging from 0.1 to 5% by weight relative to the total weight of the ready-to-use dye composition.

In another embodiment the at least one 4-electron oxidoreductase which may be used as an enzymatic oxidizing agent is chosen from at least one laccase, at least one tyrosinase, at least one catechol oxidase and at least one polyphenol oxidase enzymes.

In one embodiment according to the invention, the at least one 4-electron oxidoreductase used, is chosen from at least one laccase.

The at least one laccase may be chosen from laccases of plant origin, laccases of animal origin, laccases of fungal origin (yeasts, molds or fungi) and laccases of bacterial origin, the organisms of origin possibly being monocellular or multicellular.

In another embodiment, the at least one laccase may be obtained by biotechnological techniques.

Examples of the at least one laccase of plant origin which may be utilized in accordance with the invention, are those laccases produced by plants which carry out chlorophyll synthesis, such as, those mentioned in patent application FR—A-2 694 018 (incorporated by reference, herein).

In one embodiment of the invention, the at least one laccase is present in plant extracts chosen from: Anacardiacea, such as, *Magnifera indica, Schinus molle* and *Pleiogynium timoriense*; Podocarpacea; Rosmarinus off.; *Solanum tuberosum*; Iris sp.; Coffea sp.; *Daucus carrota*; Vincaminor; *Persea americana; Catharanthus roseus*; Musa sp.; *Malus pumila; Gingko biloba; Monotropa hypopithys* (Indian pipe), Aesculus sp.; *Acer pseudoplatanus; Prunus persica* and *Pistacia palaestina*.

Examples of at least one laccase of fungal origin, optionally obtained by biotechnological techniques, which can be used according to the invention, may comprise laccases obtained from fungi chosen from Polyporus versicolor, *Rhizoctonia praticola* and *Rhus vernicifera* as described, for example, in patent applications FR—A-2 112 549 and EP-A-504 005 (incorporated by reference, herein). Other examples of laccases obtained from fungal origin comprise the laccases described in patent applications WO 95/07988, WO 95/33836, WO 95/33837, WO 96/00290, WO 97/19998 and WO 97/19999, incorporated by reference, herein, such as, the laccases obtained from: Scytalidium, *Polyporus pinsitus, Myceliophthora thermophila, Rhizoctonia solani, Pyricularia orizae*, and variants thereof.

Additional examples may also comprise the laccases obtained from: *Trametes versicolor, Fomes fomentarius, Chaetomium thermophile, Neurospora crassa, Colorius versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens*, and variants thereof.

In one embodiment of the invention the at least one laccase of fungal origin is optionally obtained by biotechnological techniques.

In another embodiment of the invention, the enzymatic activity of the at least one laccase comprising syringaldazine among their substrates may be defined by the oxidation of syringaldazine under aerobic conditions. One Lacu unit corresponds to the amount of enzyme which catalyses the conversion of 1 mmol of syringaldazine per minute at a pH of 5.5 and at a temperature of 30° C. One U unit corresponds to the amount of enzyme which produces an absorbance delta of 0.001 per minute at a wavelength of 530 nm, using syringaldazine as a substrate, at 30° C. and at a pH of 6.5.

Additionally, the enzymatic activity of the at least one laccase used according to the invention may also be defined by the oxidation of para-phenylenediamine. One ulac unit corresponds to the amount of enzyme which produces an absorbance delta of 0.001 per minute at a wavelength of 496.5 nm, using para-phenylenediamine as substrate (64 mM), at 30° C. and at a pH of 5.

In another embodiment of the invention, the at least one 4-electron oxidoreductase is present in an amount ranging from 0.01 to 20% by weight relative to the total weight of the ready-to-use dye composition. In another embodiment, the at least one 4-electron oxidoreductase is present in an amount ranging from 0.1 to 5% by weight relative to the total weight of the ready-to-use dye composition.

When at least one laccase is used, the amount of the at least one laccase present in the ready-to-use dye composition may vary as a function of the nature of the laccase used. In one embodiment of the invention, the at least one laccase is present in an amount ranging from 0.5 to 2000 Lacu (i.e. between 10,000 to $40 \times 10^6$ U units or alternatively between 20 to $20 \times 10^6$ ulac units) per 100 g of ready-to-use dye composition.

In one embodiment of the invention, the at least one peroxidase which may be used as enzymatic oxidizing agent in the ready-to-use dye composition can be chosen from enzymes belonging to the subclass 1.11.1 described in the book Enzyme Nomenclature, Academic Press Inc., 1984 (incorporated by reference, herein). Some peroxidases belonging to this class require the presence of a donor to function. This is the case, for example, for the NADH peroxidases (1.11.1) having NADH as donor, the fatty acid peroxidases (1.11.1.3) having a fatty acid, such as, palmitate as donor, the NADPH peroxidases (1.11.1.2) having NADPH as donor, the cytochrome-c peroxidases (1.11.1.5) having ferrocytochrome-c as donor, the iodide peroxidases (1.11.1.8) having iodides as donor, the chloride peroxidases (1.11.10) having chlorides as donor, the L-ascorbate peroxidases (1.11.1.11) having L-ascorbate as donor and the glutathione peroxidases (1.11.1.9) having glutathione as donor.

Other examples of at least one peroxidase are those peroxidases belonging to the subclass 1.11.1 function without a donor other than the oxidation dye and are chosen from catalases (1.11.1.6) and simplex peroxidases (1.11.1.7).

In one embodiment of the invention, simplex peroxidases (1.11.1.7) are used.

All the peroxidases function in the presence of hydrogen peroxide, which is provided in its native form or generated in situ via an enzymatic route by at least one 2-electron oxidoreductase and its corresponding at least one donor in the presence of air.

The origin of the at least one peroxidase which may be used in the ready-to-use dye composition in accordance with the invention, is chosen from plant, animal, fungal and bacterial origin. In one embodiment of the invention, the at least one peroxidase may be obtained by biotechnological techniques.

Thus, the at least one peroxidase may be obtained, for example, from the following sources: apple, apricot, barley, black radish, beetroot, cabbage, carrot, corn, cotton, garlic, grape, mint, rhubarb, soybean, spinach, inky cap, cow's milk and microorganisms, such as, *Acetobacter peroxidans, Staphylococcus faecalis* and *Arthromyces ramosus*.

The unit of activity of simplex peroxidase (1.11.1.7) can be defined as being the amount of simplex enzyme forming 1 mg of purpurogallin from pyrogallol in 20 s at pH 6 and at 20° C. By way of example, black radish peroxidase P6782 from Sigma® has an activity of about 250 units per mg.

In one embodiment of the invention, the working concentration of this type of enzyme thus ranges from 25 to $5 \times 10^6$ units per 100 g of ready-to-use composition.

In one embodiment, the at least one peroxidase is present in an amount ranging from 0.0001 to 20% by weight relative to the total weight of the ready-to-use composition in accordance with the invention. In yet another embodiment, the at least one peroxidase is present in an amount ranging from 0.001 to 10% by weight relative to the total weight of the ready-to-use composition.

According to one embodiment, the ready-to-use dye composition in accordance with the invention contains at least one 4-electron oxidoreductase chosen from laccases.

The at least one coupler which may be present in the ready-to-use composition in accordance with the invention is chosen from the couplers conventionally used in oxidation dyeing, such as, meta-phenylenediamines, meta-aminophenols, meta-diphenols, naphthols and heterocyclic couplers, for example, chosen from pyrazolo[1,5-b]-1,2,4-triazoles, pyrazolo[3,2-c]-1,2,4-triazoles, pyrazol-5-ones, pyridines other than the pyridines of formula (I) above, such as, indoles, indolines, indazoles, benzimidazoles, benzothiazoles, benzoxazoles, 1,3-benzodioxoles and quinolines.

In one embodiment of the invention, the at least one coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(P-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2-amino-3-hydroxypyridine, 3,6-dimethylpyrazolo[3,2-c]-1,2,4-triazol, 2,6-dimethylpyrazolo[1,5-b]-1,2,4-triazole, and acid addition salts thereof.

In one embodiment of the invention, the at least one coupler is present in an amount ranging from 0.0001 to 10% by weight relative to the total weight of the ready-to-use dye composition. In another embodiment, the at least one coupler is present in an amount ranging from 0.005 to 5% by weight relative to the total weight of the ready-to-use dye composition.

In another embodiment of the invention, the ready-to-use dye composition may further comprise at least one direct dye, used for example, to modify the shades or to enrich them with glints.

In general, the acid addition salts which can be used in the context of the dye compositions of the invention (pyridines of formula (I), oxidation bases and couplers) are chosen, for example, from hydrochlorides, hydrobromides, sulphates, tartrates, lactates and acetates.

In one embodiment the medium which is suitable for dyeing (or support) for the ready-to-use dye composition in accordance with the invention comprises water. In another embodiment of the invention, the medium suitable for dyeing comprises a mixture of water and at least one organic solvent to dissolve the compounds which would not be sufficiently soluble in water. By way of organic solvents, mention may be made, for example, of $C_1$–$C_4$ alkanols, such as ethanol and isopropanol; glycerol; glycols and glycol ethers, such as, 2-butoxyethanol, propylene glycol, propylene glycol monomethyl ether, diethylene glycol monoethyl ether and monomethyl ether, and aromatic alcohols, such as, benzyl alcohol and phenoxyethanol, similar products and mixtures thereof.

In one embodiment, the at least one organic solvent may be present in amount ranging from 1 to 40% by weight relative to the total weight of the dye composition. In another embodiment, the at least one organic solvent may be present in an amount ranging from 5 to 30% by weight relative to the total weight of the dye composition.

The pH of the ready-to-use composition in accordance with the invention is chosen such that the enzymatic activity of the enzyme used is sufficient. In one embodiment of the invention, the pH ranges from 5 to 11. In another embodiment of the invention, the pH ranges from 6.5 to 10. The pH may be adjusted to the desired value using acidifying and alkalinizing agents usually used for dyeing keratinous fibers.

Among the acidifying agents, mention may be made, by way of example, of inorganic and organic acids, chosen from hydrochloric acid, orthophosphoric acid, sulphuric acid, carboxylic acids, such as, acetic acid, tartaric acid, citric acid and lactic acid, and sulfuric acids.

Among the alkalinizing agents, mention may be made, by way of example, of alkalinizing agents chosen from aqueous ammonia, alkali metal carbonates, alkanolamines, such as, mono-, di- and triethanolamines, 2-methyl-2-aminopropanol and derivatives thereof, sodium hydroxide, potassium hydroxide and the compounds of formula (VI) below:

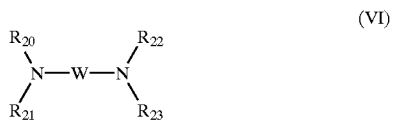

(VI)

wherein:
W is a propylene residue, optionally substituted with a group chosen from a hydroxyi group and a ($C_1$–$C_4$) alkyl group, $R_{20}$, $R_{21}$, $R_{22}$ and $R_{23}$, which are identical or different, are each chosen from a hydrogen atom, a ($C_1$–$C_4$)alkyl group and a ($C_1$–$C_4$)hydroxyalkyl group.

The ready-to-use dye composition in accordance with the invention may also comprise at least one adjuvant used conventionally in compositions for the dyeing of the hair, such as, anionic, cationic, nonionic, amphoteric and zwitterionic surfactants: anionic, cationic, nonionic, amphoteric and zwitterionic polymers; inorganic and organic thickeners; antioxidants; penetration agents; sequestering agents; fragrances; buffers; dispersing agents; and conditioning agents, for example, modified and unmodified, non-volatile and volatile silicones, film-forming agents, ceramides, preserving agents and opacifying agents.

Needless to say, a person skilled in the art may choose these optional, complementary compounds such that the advantageous properties intrinsically associated with the ready-to-use dye composition in accordance with the invention are not substantially adversely affected by the additions envisaged.

The ready-to-use dye composition in accordance with the invention may be provided in various forms, such as, optionally pressurized, liquids, creams, and gels, or in any other form suitable for dyeing keratinous fibers, such as human hair. In one embodiment of the invention, the at least one oxidation dye and the at least one enzymatic oxidizing agent are present in the same ready-to-use composition, and consequently the said composition should be free of gaseous oxygen, so as to avoid any premature oxidation of the oxidation dyes.

Another embodiment of the invention, is a method of oxidation dyeing keratinous fibers, for example, human keratinous fibers such as hair, using the ready-to-use dye composition as defined above.

According to this method, at least one ready-to-use dye composition, as defined above, may be applied to the fibers for a period of time sufficient to develop the desired coloration, after which the fibers may be rinsed, washed with shampoo, rinsed again and dried.

In one embodiment, the time required to develop the coloration on the keratinous fibers ranges from 3 to 60 minutes. In another embodiment of the invention, the time required to develop the coloration on the keratinous fibers ranges from 5 to 40 minutes.

According to one embodiment of the invention, the method previously described may also include a preliminary step which comprises separately storing, on the one hand, a composition (A) comprising, in a medium suitable for dyeing, at least one oxidation dye chosen from pyridines of formula (I) as defined previously, and, on the other hand, a composition (B) comprising, in a medium suitable for dyeing, at least one enzymatic oxidizing agent chosen from a) at least one 2-electron oxidoreductase in the presence of its corresponding at least one donor, b) at least one 4-electron oxidoreductase, c) at least one peroxidase, and mixing said composition A and said composition B together at the time of use, and then applying this mixture to the keratinous fibers.

Another embodiment of the invention is a multi-compartment dyeing device, dyeing "kit" or any other multi-compartment packaging system, wherein a first compartment comprises composition (A) as defined above and a second compartment comprises composition (B) as defined above. These devices may be equipped with a means to deliver the desired mixture to the hair, such as the devices described in patent FR-2,586,913, which is incorporated by reference herein.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

The examples which follow are intended to illustrate the invention without, however, limiting its scope.

DYEING EXAMPLES 1 to 9

Table 1 shows the prepared ready-to-use dye compositions (contents in grams):

TABLE 1

DYEING EXAMPLES 1–9

| EXAMPLE | 1 | 2 | 3 | 4 | 5 | 6 | 7 | 8 | 9 |
|---|---|---|---|---|---|---|---|---|---|
| 2,6-Dimethoxy-3,5-diaminopyridine dihydrochloride (oxidation dye of formula (I)) | 0.636 | 0.636 | 0.636 | — | 0.636 | — | — | — | — |
| 2-Methylamino-3-amino-6-methoxypyridine (oxidation dye of formula (I)) | — | — | — | 0.732 | 0.732 | — | — | — | — |
| 2,3-Diamino-6-methoxypyridine dihydrochloride (oxidation dye of formula (I)) | — | — | — | — | — | 0.636 | 0.636 | 0.636 | 0.636 |
| para-Phenylenediamine (oxidation base) | 0.324 | — | — | — | — | 0.324 | — | — | — |
| 2-Aminophenol (oxidation base) | — | — | 0.327 | 0.327 | — | — | — | — | 0.327 |
| para-Aminophenol (oxidation base) | — | — | — | — | — | — | 0.327 | — | — |
| 4,5-Diamino-1-ethyl-3-methylpyrazole dihydrochloride (oxidation base) | — | 0.639 | — | — | — | — | — | 0.639 | — |
| Common dye support | (*) | (*) | (*) | (*) | (*) | (*) | (*) | (*) | (*) |
| pH agent (citric acid or 2-amino-2-methyl-1-propanol) qs | pH 7 | pH 7 | pH 7 | pH 7 | pH 7 | pH 7 | pH 7 | pH 7 | pH 7 |
| Distilled water qs | 100 g | 100 g | 100 g | 100 g | 100 g | 100 g | 100 g | 100 g | 100 g |

*Common dye support

COMMON DYE SUPPORT USED IN EXAMPLES 1–9 OF TABLE 1:

| | |
|---|---|
| Carboxymethylchitosan containing 84% active material (A.M.) in water, sold under the name Olevasan ® by the company Sino-Lion | 2.0 g |
| Hydroxypropyl guar trimethylammonium chloride sold under the name Jaguar C13S ® by the company Rhodia Chimie | 2.0 g |
| Polyglyceryl monooleate (10 mol) sold under the name Decaglyn 10 ® by the company Nikko | 1.0 g |
| N-Acetyl-L-cysteine | 0.05 g |
| Laccase | 5.0 g |

The amount of laccase used in the dye support corresponds to 5 360 000 ulac units per 100 g of ready-to-use dye composition.

The ready-to-use dye compositions described above were applied to locks of natural grey hair containing 90% white hairs, for 30 minutes at room temperature. The hair was then rinsed, washed with a standard shampoo and then dried.

The hair was dyed in the shades listed in Table 2.

TABLE 2

Shades of Dyed Hair

| EXAMPLE | SHADE OBTAINED |
|---|---|
| 1 | Black-blue |
| 2 | Red-mahogany |
| 3 | Bronze-green |
| 4 | Slightly matt intense golden |
| 5 | Golden-green |
| 6 | Black-violet |
| 7 | Ash golden bronze-green |
| 8 | Intense blue-green |
| 9 | Bronze green-golden |

EXAMPLE 10

The ready-to-use composition below was prepared:

| | |
|---|---|
| 2,6-Dimethoxy-3,5-diaminopyridine dihydrochloride (oxidation dye of formula (I)) | 0.726 g |
| para-Phenylenediamine (oxidation base) | 0.324 g |
| Uric acid | 1.0 g |
| Uricase | 1.0 g |
| Oxyethylenated methacrylic acid/ethyl acrylate/stearyl methacrylate terpolymer sold under the name Aculyn 22 ® by the company Rohm & Haas | 2.5 g |
| Polyglyceryl monooleate (10 mol) sold under the name Decaglyn 10 ® by the company Nikko | 1.0 g |
| N-Acetyl-L-cystein | 0.1 g |
| 2-Amino-2-methyl-1-propanol qs | pH = 9.5 |
| Distilled water qs | 100 g |

The amount of uricase used in this ready-to-use composition corresponds to 20 000 U units per 100 g of ready-to-use composition.

The ready-to-use dye composition described above was applied to locks of natural grey hair containing 90% white hairs for 30 minutes at room temperature. The hair was then rinsed, washed with a shampoo, rinsed again and then dried.

The hair was dyed in an intense ash-blue shade.

What is claimed is:

1. Ready-to-use composition for the oxidation dyeing of keratinous fibers, comprising, in a medium suitable for dyeing:

(a) at least one oxidation dye chosen from the pyridines of formula (I), and acid addition salts thereof:

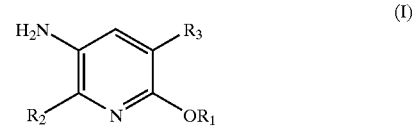

(I)

wherein:

$R_1$ is chosen from a $(C_1-C_4)$alkyl group, a $(C_1-C_4)$ monohydroxyalkyl group, and a $(C_2-C_4)$ polyhydroxyalkyl group, $R_2$ is chosen from a $(C_1-C_4)$alkoxy group, a $(C_1-C_4)$ monohydroxyalkoxy group, a $(C_2-C_4)$ polyhydroxyalkoxy group, an amino group, a mono($C_1$–$C_4$)alkylamino group, a di-($C_1$–$C_4$)alkylamino group, a monophenylamino group, a monohydroxyphenylamino group, a monoalkoxyphenylamino group, a monohydroxy($C_1$–$C_4$)alkylamino group, a dihydroxy-($C_1$–$C_4$)alkylamino group, a monohydroxy-($C_2$–$C_4$)alkylamino group, a dihydroxy-($C_2$–$C_4$)alkylamino group, a ($C_1$–$C_4$)alkylmonohydroxy-($C_1$–$C_4$)alkylamino group and a ($C_1$–$C_4$)alkylpolyhydroxy($C_2$–$C_4$)alkylamino group, $R_3$ is chosen from a hydrogen atom, an amino group, a mono($C_1$–$C_4$)alkylamino group, a monohydroxy($C_1$–$C_4$)alkylamino group and a mono(polyhydroxy($C_2$–$C_4$)alkyl)amino group;

provided that: when $R_2$ is chosen from a ($C_1$–$C_4$)alkoxy group, a ($C_1$–$C_4$)monohydroxyalkoxy group and a ($C_2$–$C_4$)polyhydroxyalkoxy group, then $R_3$ is a hydrogen atom; and further provided that the at least one oxidation dye can be 2,6-dimethoxy-3,5-diaminopyridine; and (b) at least one enzymatic oxidizing agent chosen from:
(i) a system comprising at least one 2-electron oxidoreductase and its corresponding at least one donor,
(ii) at least one 4-electron oxidoreductase, and
(iii) at least one peroxidase.

2. A composition according to claim 1, wherein said at least one oxidation dye of formula (I) is chosen from: 2,6-dimethoxy-3,5-diaminopyridine, 2,3-diamino-6-methoxypyridine, 2-methylamino-3-amino-6-methoxypyridine, 2-(2'-hydroxyphenyl)amino-3-amino-6-methoxypyridine-2-(4'-hydroxyphenyl)amino-3-amino-6-methoxypyridine, 2-(4'-methoxyphenyl)amino-3-amino-6-methoxypyridine, 2-phenylamino-3-amino-6-methoxypyridine, and acid addition salts thereof.

3. A composition according to claim 2, wherein said at least one oxidation dye of formula (I) is chosen from 2,6-dimethoxy-3,5-diaminopyridine and at least one acid addition salts thereof.

4. A composition according to claim 1, wherein said at least one oxidation dye of formula (I) is present in an amount ranging from 0.0001 to 10% by weight relative to the total weight of the dye composition.

5. A composition according to claim 4, wherein said at least one oxidation dye of formula (I) is present in an amount ranging from 0.005 to 5% by weight relative to the total weight of the dye composition.

6. A composition according to claim 1, further comprising at least one oxidation base.

7. A composition according to claim 6, wherein said at least one oxidation base is chosen from para-phenylenediamines, double bases, para-aminophenols, ortho-aminophenols and heterocyclic oxidation bases.

8. A composition according to claim 7, wherein said para-phenylenediamines are chosen from the compounds of formula (II) and acid addition salts thereof:

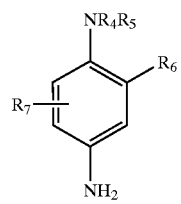

(II)

wherein:
$R_4$ is chosen from a hydrogen atom, a ($C_1$–$C_4$)alkyl group optionally substituted with a nitrogenous group, a ($C_1$–$C_4$)monohydroxyalkyl group, a ($C_2$–$C_4$)polyhydroxyalkyl group, a ($C_1$–$C_4$)alkoxy($C_1$–$C_4$)alkyl group, a phenyl group and a 4'-aminophenyl group;

$R_5$ is chosen from a hydrogen atom, a $C_1$–$C_4$ alkyl group optionally substituted with a nitrogenous group, a $C_1$–$C_4$ monohydroxyalkyl group, a $C_2$–$C_4$polyhydroxyalkyl group, and a ($C_1$–$C_4$)alkoxy($C_1$–$C_4$)alkyl group;

$R_6$ is chosen from a hydrogen atom, a halogen atom, a ($C_1$–$C_4$)alkyl group, a ($C_1$–$C_4$)monohydroxyalkyl group, a ($C_1$–$C_4$)hydroxyalkoxy group, an acetylamino($C_1$–$C_4$)alkoxy group, a($C_1$–$C_4$) mesylaminoalkoxy group and a carbamoylamino ($C_1$–$C_4$)alkoxy group, $R_7$ is chosen from a hydrogen atom, a halogen atom and a $C_1$–$C_4$ alkyl group.

9. A composition according to claim 8, wherein said nitrogenous groups are chosen from amino, mono($C_1$–$C_4$) alkylamino, di($C_1$–$C_4$)alkylamino, tri($C_1$–$C_4$)-alkylamino, monohydroxy($C_1$–$C_4$)alkylamino, imidazolinium and ammonium groups.

10. A composition according to claim 7, wherein said para-phenylenediamines of formula (II) are chosen from para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β3-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid addition salts thereof.

11. A composition according to claim 10, wherein said para-phenylenediamines of formula (II) are chosen from para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine and acid addition salts thereof.

12. A composition according to claim 7, wherein said double bases are chosen from compounds of formula (III) and acid addition salts thereof:

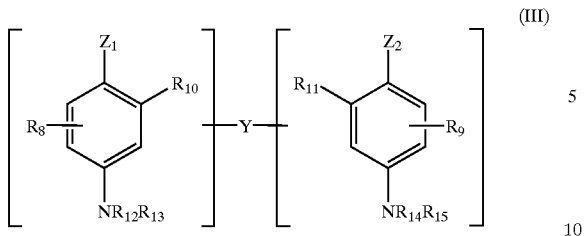

(III)

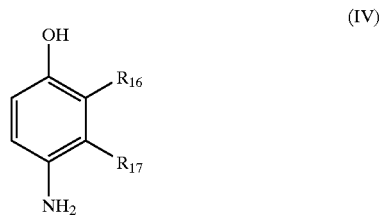

(IV)

wherein:
a linker arm Y chosen from linear and branched alkylene groups comprising from 1 to 14 carbon atoms optionally substituted with at least one group chosen from hydroxyl and $(C_1-C_6)$alkoxy groups, wherein said linear and branched alkylene groups are optionally interrupted by or terminated by at least one group chosen from nitrogenous groups and heteroatoms chosen from oxygen, sulfur, and nitrogen atoms;

$Z_1$, and $Z_2$, which are identical or different, are each chosen from a hydroxyl group and an amino group optionally substituted with a group chosen from a $(C_1-C_4)$alkyl group and said linker arm Y;

$R_8$ and $R_9$ which are identical or different, are each chosen from a hydrogen atom, a halogen atom, a $(C_1-C_4)$alkyl group, a $(C_1-C_4)$monohydroxyalkyl group, a $(C_2-C_4)$polyhydroxyalkyl group, a $(C_1-C_4)$ aminoalkyl group and said linker arm Y;

$R_{10}$, $R_{11}$, $R_{12}$, $R_{13}$, $R_{14}$ and $R_{15}$, which are identical or different, are each chosen from a hydrogen atom, said linker arm Y and a $(C_1-C_4)$alkyl group;

provided that: said compounds of formula (III) contain only one said linker arm Y per molecule.

13. A composition according to claim 12, wherein said nitrogenous groups are chosen from amino, mono($C_1-C_4$) alkylamino, di($C_1-C_4$)alkylamino, tri($C_1-C_4$)-alkylamino, monohydroxy($C_1-C_4$)alkylamino, imidazolinium and ammonium groups.

14. A composition according to claim 12, wherein said double bases of formula (III) are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)-tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and addition salts thereof.

15. A composition according to claim 14, wherein said double bases of formula (III) are chosen from N,N'-bis(β-hydroxyethyl)-N,N'-bis(4'-aminophenyl)-1,3-di aminopropanol, 1,8-bis(2,5-diaminophenoxy)-3,5-dioxaoctane, and acid addition salts thereof.

16. A composition according to claim 7, wherein said para-aminophenols are chosen from the compounds of formula (IV) and acid addition salts thereof:

wherein:
$R_{16}$ is chosen from a hydrogen atom, a halogen atom, a $(C_1-C_4)$alkyl group, a $(C_1-C_4)$monohydroxyalkyl group, a($C_1-C_4$)alkoxy($C_1-C_4$)alkyl group, a $(C_1-C_4)$aminoalkyl group and a hydroxy$(C_1-C_4)$alkylamino$(C_1-C_4)$alkyl group, $R_{17}$ is chosen from a hydrogen atom, a halogen atom, a $(C_1-C_4)$alkyl group, $(C_1-C_4)$monohydroxyalkyl group, $(C_2-C_4)$polyhydroxyalkyl group, $(C_1-C_4)$ aminoalkyl group, $(C_1-C_4)$cyanoalkyl group and a $(C_1-C_4)$alkoxy-$(C_1-C_4)$alkyl group, provided that: at least one of $R_{16}$ and $R_{17}$ is a hydrogen atom.

17. A composition according to claim 16, wherein said para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid addition salts thereof.

18. A composition according to claim 7, wherein said ortho-aminophenols are chosen from 2-aminophenol, 2-amino-5-methylphenol, 2-amino-6-methylphenol and 5-acetamido-2-aminophenol, and acid addition salts thereof.

19. A composition according to claim 7, wherein said heterocyclic oxidation bases are chosen from pyridine derivatives, pyrimidine derivatives, pyrazolopyrimidine derivatives, pyrazole derivatives and acid addition salts thereof.

20. A composition according to claim 19, wherein said pyridine derivatives are chosen from 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine 3,4-diaminopyridine, and acid addition salts thereof.

21. A composition according to claim 19, wherein said pyrimidine derivatives are chosen from 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and acid addition salts thereof.

22. A composition according to claim 19, wherein said pyrazolopyrimidine derivatives are chosen from pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimdine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7- imidazolylpropylaminopyrazolo[1,5-a]pyrimidine, a corresponding tautomeric form thereof, when a tautomeric equilibrium exits, and acid addition salts thereof.

23. A composition according to claim 19, wherein said pyrazole derivatives are chosen from 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethyl pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and acid addition salts thereof.

24. A composition according to claim 6, wherein said at least one oxidation base is present in an amount ranging from 0.0005 to 12% by weight relative to the total weight of the ready-to-use dye composition.

25. A composition according to claim 24, wherein said at least one oxidation base is present in an amount ranging from 0.005 to 8% by weight relative to the total weight of the ready-to-use dye composition.

26. A composition according to claim 1, wherein said at least one 2-electron oxidoreductase is chosen from pyranose oxidases, glucose oxidases, glycerol oxidases, lactate oxidases, pyruvate oxidases, uricases, choline oxidases, sarcosine oxidases and bilirubin oxidases.

27. A composition according to claim 26, wherein said at least one 2-electron oxidoreductase is chosen from uricases of animal, uricases of microbiological and uricases of biotechnological origin.

28. A composition according to claim 27, wherein said at least one 2-electron oxidoreductase is chosen from uricases extracted from boar's liver, *Arthrobacter globiformis* and *Aspergillus flavus*.

29. A composition according to claim 1, wherein said at least one 2-electron oxidoreductase is present in an amount ranging from 0.01 to 20% by weight relative to the total weight of the ready-to-use dye composition.

30. A composition according to claim 29, wherein said at least one 2-electron oxidoreductase is present in an amount ranging from 0.1 to 10% by weight relative to the total weight of the ready-to-use dye composition.

31. A composition according to claim 30, wherein said at least one 2-electron oxidoreductase is present in an amount ranging from 0.1 to 5% by weight relative to the total weight of the ready-to-use dye composition.

32. A composition according to claim 1, wherein said at least one 2-electron oxidoreductase is present in an amount ranging from 10 to $10^8$ units U per 100 g of ready-to-use dye composition.

33. A composition according to claim 1, wherein said at least one donor is present in an amount ranging from 0.01 to 20% by weight relative to the total weight of the ready-to-use dye composition.

34. A composition according to claim 33, wherein said at least one donor is present in an amount ranging from 0.1 to 5% by weight relative to the total weight of the ready-to-use dye composition.

35. A composition according to claim 1, wherein said at least one 4-electron oxidoreductase is chosen from at least one laccase, at least one tyrosinase, at least one catechol oxidase and at least one polyphenol oxidase.

36. A composition according to claim 35, wherein said at least one 4-electron oxidoreductase is chosen from at least one laccase.

37. A composition according to claim 36, wherein said at least one laccase is chosen from laccases of plant origin, laccases of animal origin, laccases of fungal origin and laccases of bacterial origin.

38. A composition according to claim 36, wherein said at least one laccase is chosen from laccases obtained by biotechnological techniques.

39. A composition according to claim 37, wherein said at least one laccase of plant origin is chosen from: Anacardiacea chosen from *Magnifera indica, Schinus molle* and *Pleiogynium timoriense*; Podocarpacea; Rosmarinus off.; *Solanum tuberosum*; Iris sp.; Coffea sp.; *Daucus carrota; Vinca minor;* and *Persea americana; Catharanthus roseus*; Musa sp.; *Malus pumila; Gingko biloba; Monotropa hypopithys* (Indian pipe), Aesculus sp.; *Acer pseudoplatanus; Prunus persica* and *Pistacia palaestina*.

40. A composition according to claim 37, wherein said at least one laccase of fungal origin is chosen from *Polyporus versicolor, Rhizoctonia praticola, Rhus vemicifera,* Scytalidium, *Polyporus pinsitus, Myceliophthora thermophila, Rhizoctonia solani, Pyricularia orizae, Trametes versicolor, Fomes fomentarius, Chaetomium thermophile, Neurospora crassa, Colorius versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens*, and variants thereof.

41. A composition according to claim 37, wherein said at least one laccase of fungal origin is obtained by biotechnological techniques.

42. A composition according to claim 36, wherein said at least one laccase is present in an amount ranging from 0.5 to 2000 Lacu per 100 g of ready-to-use dye composition.

43. A composition according to claim 1, wherein said at least one 4-electron oxidoreductase is present in an amount ranging from 0.01 to 20% by weight relative to the total weight of the ready-to-use dye composition.

44. A composition according to claim 43, wherein said at least one 4-electron oxidoreductase is present in an amount ranging from 0.1 to 5% by weight relative to the total weight of the ready-to-use dye composition.

45. A composition according to claim 1, wherein said at least one peroxidase is chosen from NADH peroxidases having NADH as donor, fatty acid peroxidases having a fatty acid as a donor, NADPH peroxidases having NADPH as donor, cytochrome-c peroxidases having ferrocytochrome c as donor, iodide peroxidases having iodides as donor, chloride peroxidases having chlorides as donor, L-acorbate peroxidases having L-ascorbate as donor and glutathione peroxidases having glutathione as donor, catalases and peroxidases.

46. A composition according to claim 45, wherein said peroxidases are present in an amount ranging from 0.1 to $5\times10^6$ units per 100 g of the ready-to-use dye composition.

47. A composition according to claim 1, wherein said at least one peroxidase is chosen from peroxidases of plant origin, peroxidases of animal origin, peroxidases of fungal origin and peroxidases of bacterial origin.

48. A composition according to claim 1, wherein said at least one peroxidase is chosen from peroxidases obtained by biotechnological techniques.

49. A composition according to claim 1, wherein said at least one peroxide is present in an amount ranging from 0.0001 to 20% by weight relative to the total weight of the ready-to-use dye composition.

50. A composition according to claim 1, wherein said at least one peroxidase is present in an amount ranging from 0.001 to 10% by weight relative to the total weight of the ready-to-use dye composition.

51. A composition according to claim 1, further comprising at least one coupler is chosen from meta-phenylenediamines, meta-aminophenols, meta-diphenols, naphthols, heterocyclic couplers chosen from pyrazolo[1,5-b]-1,2,4-triazoles, pyrazolo[3,2-c]-1,2,4-triazoles, and pyrazol-5-ones, pyridines other than the pyridines of formula (I) chosen from indoles, indolines, indazoles, benzimidazoles, benzothiazoles, benzoxazoles, 1,3-benzodioxoles and quinolines.

52. A composition according to claim 51, wherein said at least one coupler is chosen from 2-methyl-5-aminophenol, 5-N-(p-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2-amino-3-hydroxypyridine, 3,6-dimethylpyrazolo[3,2-c]-1,2,4-triazole 2,6-dimethylpyrazolo[1,5-b]-1,2,4-triazole, and acid addition salts thereof.

53. A composition according to claim 51, wherein said at least one coupler is present in an amount ranging from 0.0001 to 10% by weight relative to the total weight of the ready-to-use dye composition.

54. A composition according to claim 53, wherein said at least one coupler is present in an amount ranging from 0.005 to 5% by weight relative to the total weight of the ready-to-use dye composition.

55. A composition according to claim 1 further comprising at least one direct dye.

56. A composition according to claim 1, wherein said acid addition salts are chosen from hydrochlorides, hydrobromides, sulphates, tartrates, lactates and acetates.

57. A composition according to claim 1, wherein said medium suitable for dyeing, is chosen from media comprising water; and media comprising at least one organic solvent.

58. A composition according to claim 57, wherein said at least one organic solvent is chosen from $C_1$–$C_4$ alkanols; glycerol; glycols and glycol ethers; and aromatic alcohols.

59. A composition according to claim 58, wherein said $C_1$–$C_4$ alkanols are chosen from ethanol and isopropanol.

60. A composition according to claim 58, wherein said glycols and glycol ethers are chosen from 2-butoxyethanol, propylene glycol, propylene glycol monomethyl ether, diethylene glycol monoethyl ether and monomethyl ether.

61. A composition according to claim 58, wherein said aromatic alcohols are chosen from benzyl alcohol and phenoxyethanol.

62. A composition according to claim 57, wherein said at least one organic solvent is present in an amount ranging from 1 to 40% by weight relative to the total weight of the ready-to-use dye composition.

63. A composition according to claim 62, wherein said at least one organic solvent is present in an amount ranging from 5 to 30% by weight relative to the total weight of the ready-to-use dye composition.

64. A composition according to claim 1, wherein said composition has a pH ranging from 5 to 11.

65. A composition according to claim 64, wherein said composition has a pH ranging from 6.5 to 10.

66. A composition according to claim 64, further comprising at least one agent for adjusting pH chosen from acidifying and alkalinizing agents.

67. A composition according to claim 66, wherein said acidifying agents are chosen from inorganic and organic acids.

68. A composition according to claim 67, wherein said inorganic and organic acids are chosen from hydrochloric, orthophosphoric, sulfuric, and carboxylic acids.

69. A composition according to claim 68, wherein said carboxylic acids are chosen from acetic, tartaric, citric, lactic and sulfonic acids.

70. A composition according to claim 66, wherein said alkalinizing agents chosen from aqueous ammonia, alkali metal carbonates, alkanolamines, sodium hydroxides, potassium hydroxides and the compounds of formula (VI) below:

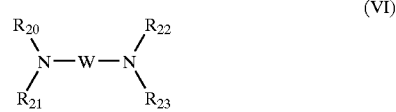

wherein:
W is a propylene residue, optionally substituted with a group chosen from a hydroxyl group and a ($C_1$–$C_4$) alkyl group, $R_{20}$, $R_{21}$, $R_{22}$ and $R_{23}$, which are identical or different, are each chosen from a hydrogen atom, and a ($C_1$–$C_4$)alkyl and ($C_1$–$C_4$) hydroxyalkyl groups.

71. A composition according to claim 70, wherein said alkanolamines are chosen from mono-, di- and triethanolamine, 2-methyl-2-aminopropanol and derivatives thereof.

72. A composition according to claim 1, further comprising at least one adjuvant used in hair dyeing compositions.

73. A composition according to claim 72, wherein said at least one adjuvant is chosen from anionic, cationic, nonionic, amphoteric and zwitterionic surfactants; anionic, cationic, nonionic, amphoteric and zwitterionic polymers; inorganic and organic thickeners; antioxidants; penetration agents; sequestering agents; fragrances; buffers; dispersing agents; and conditioning agents.

74. A composition according to claim 73 wherein said conditioning agents are chosen from modified and unmodified, non-volatile and volatile silicones, film-forming agents, ceramides, preserving agents and opacifying agents.

75. A composition according to claim 1, wherein said composition is a liquid, a cream a gel, or any form suitable for dyeing keratinous fibers.

76. A composition according to claim 74, wherein said keratinous fibers are human hair.

77. A composition according to claim 1, wherein said composition is free of gaseous oxygen.

78. A process for oxidation dyeing keratinous fibers comprising:
(1) applying to said fibers at least one ready-to-use dyeing composition comprising, in a medium suitable for dyeing:
(a) at least one oxidation dye chosen from the pyridines of formula (I), and acid addition salts thereof:

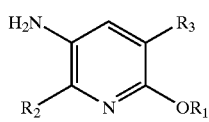

(I)

wherein:
$R_1$ is chosen from a $(C_1-C_4)$alkyl group, a $(C_1-C_4)$ monohydroxyalkyl group, and a $(C_2-C_4)$ polyhydroxyalkyl group,
$R_2$ is chosen from a $(C_1-C_4)$alkoxy group, a $(C_1-C_4)$ monohydroxyalkoxy group, a $(C_2-C_4)$ polyhydroxyalkoxy group, an amino group, a mono $(C_1-C_4)$alkylamino group, a di-$(C_1-C_4)$alkylamino group, a monophenylamino group, a monohydroxyphenylamino group, a monoalkoxyphenylamino group, a monohydroxy$(C_1-C_4)$alkylamino group, a dihydroxy-$(C_1-C_4)$alkylamino group, a monohydroxy-$(C_2-C_4)$alkylamino group, a dihydroxy-$(C_2-C_4)$alkylamino group, a $(C_1-C_4)$ alkylmonohydroxy-$(C_1-C_4)$alkylamino group and a $(C_1-C_4)$alkyl-polyhydroxy$(C_2-C_4)$alkylamino group,
$R_3$ is chosen from a hydrogen atom, an amino group, a Mono$(C_1-C_4)$alkylamino group, a monohydroxy $(C_1-C_4)$alkylamino group and a mono(polyhydroxy $(C_2-C_4)$alkyl)amino group;
provided that: when $R_2$ is chosen form a $(C_1-C_4)$alkoxy group, a $(C_1-C_4)$monohydroxyalkoxy group and a $(C_2-C_4)$polyhydroxyalkoxy group, then $R_3$ is a hydrogen atom; and
further provided that the at least one oxidation dye can be 2,6-dimethoxy-3,5-diaminopyridine; and
(b) at least one enzymatic oxidizing agent chosen from:
(i) a system comprising at least one 2-electron oxidoreductase and its corresponding at least one donor,
(ii) at least one 4-electron oxidoreductase, and
(iii) at least one peroxidase;
(2) developing a color; and
(3) rinsing said keratinous fibers.

79. A process for oxidation dyeing keratinous fibers according to claim 78, further comprising:
washing said keratinous fibers with shampoo;
rinsing said keratinous fibers; and
drying said keratinous fibers.

80. A process for oxidation dyeing keratinous fibers according to claim 78, wherein the time for developing a color ranges from 3 to 60 minutes.

81. A process for oxidation dyeing keratinous fibers according to claim 80, wherein the time for developing a color ranges from 5 to 40 minutes.

82. A process for oxidation dyeing keratinous fibers comprising:
(1) storing a composition (A) comprising, in a medium suitable for dyeing:
at least one oxidation dye chosen from the pyridines of formula (I), and acid addition salts thereof:

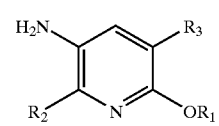

(I)

wherein:
$R_1$ is chosen from a $(C_1-C_4)$alkyl group, a $(C_1-C_4)$ monohydroxyalkyl group, and a $(C_2-C_4)$ polyhydroxyalkyl group,
$R_2$ is chosen from a $(C_1-C_4)$alkoxy group, a $(C_1-C_4)$ monohydroxyalkoxy group, a $(C_2-C_4)$ polyhydroxyalkoxy group, an amino group, a mono $(C_1-C_4)$alkylamino group, a di-$(C_1-C_4)$alkylamino group, a monophenylamino group, a monohydroxyphenylamino group, a monoalkoxyphenylamino group, a monohydroxy$(C_1-C_4)$alkylamino group, a dihydroxy-$(C_1-C_4)$alkylamino group, a monohydroxy-$(C_2-C_4)$alkylamino group, a dihydroxy-$(C_2-C_4)$alkylamino group, a $(C_1-C_4)$ alkylmonohydroxy-$(C_1-C_4)$alkylamino group and a $(C_1-C_4)$alkyl-polyhydroxy$(C_2-C_4)$alkylamino group,
$R_3$ is chosen from a hydrogen atom, an amino group, a mono$(C_1-C_4)$alkylamino group, a monohydroxy $(C_1-C_4)$alkylamino group and a mono(polyhydroxy $(C_2-C_4)$alkyl)amino group;
provided that: when $R_2$ is chosen form a $(C_1-C_4)$alkoxy group, a $(C_1-C_4)$monohydroxyalkoxy group and a $(C_2-C_4)$polyhydroxyalkoxy group, then $R_3$ is a hydrogen atom; and
further provided that the at least one oxidation dye can be 2,6-dimethoxy-3,5-diaminopryidine;
(2) storing, separately from said composition (A), a composition (B) comprising, in a medium suitable for dyeing:
at least one enzymatic oxidizing agent chosen from:
(i) a system comprising at least one 2-electron oxidoreductase and its corresponding at least one donor,
(ii) at least one 4-electron oxidoreductase, and
(iii) at least one peroxidase;
(3) mixing said composition (A) and said composition (B).

83. A process for oxidation dyeing keratinous fibers according to claim 82, wherein the time for developing a color ranges from 3 to 60 minutes.

84. A process for oxidation dyeing keratinous fibers according to claim 82, wherein the time for developing a color ranges from 3 to 60 minutes.

85. A process for oxidation dyeing keratinous fibers according to claim 84, wherein the time for developing a color ranges from 5 to 40 minutes.

86. A kit comprising two compartments, wherein:
(1) a first compartment comprises in a medium suitable for dyeing keratinous fibers:
at least one oxidation dye chosen from the pyridines of formula (I), and acid addition salts thereof:

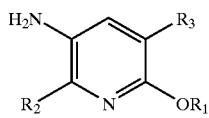

(I)

wherein:
- $R_1$ is chosen from a ($C_1$–$C_4$)alkyl group, a ($C_1$–$C_4$) monohydroxyalkyl group, and a ($C_2$–$C_4$) polyhydroxyalkyl group,
- $R_2$ is chosen from a ($C_1$–$C_4$)alkoxy group, a ($C_1$–$C_4$) monohydroxyalkoxy group, a ($C_2$–$C_4$) polyhydroxyalkoxy group, an amino group, a mono($C_1$–$C_4$)alkylamino group, a di-($C_1$–$C_4$)alkylamino group, a monophenylamino group, a monohydroxyphenylamino group, a monoalkoxyphenylamino group, a monohydroxy($C_1$–$C_4$)alkylamino group, a dihydroxy-($C_1$–$C_4$)alkylamino group, a monohydroxy-($C_2$–$C_4$)alkylamino group, a dihydroxy-($C_2$–$C_4$)alkylamino group, a ($C_1$–$C_4$) alkylmonohydroxy-($C_1$–$C_4$)alkylamino group and a ($C_1$–$C_4$)alkyl-polyhydroxy($C_2$–$C_4$)alkylamino group,
- $R_3$ is chosen from a hydrogen atom, an amino group, a mono($C_1$–$C_4$)alkylamino group, a monohydroxy ($C_1$–$C_4$)alkylamino group and a mono(polyhydroxy ($C_2$–$C_4$)alkyl)amino group;
- provided that: when $R_2$ is chosen form a ($C_1$–$C_4$)alkoxy group, a ($C_1$–$C_4$)monohydroxyalkoxy group and a ($C_2$–$C_4$)polyhydroxyalkoxy group, then $R_3$ is a hydrogen atom; and
- further provided that the at least one oxidation dye can be 2,6-dimethoxy-3,5-diaminopyridine; and (2) a second compartment comprises in a medium suitable for dyeing, a composition (B) comprising:
at least one enzymatic oxidizing agent chosen from:
 (i) a system comprising at least one 2-electron oxidoreductase and its corresponding at least one donor,
 (ii) at least one 4-electron oxidoreductase, and
 (iii) at least one peroxidase.

\* \* \* \* \*

UNITED STATES PATENT AND TRADEMARK OFFICE
CERTIFICATE OF CORRECTION

PATENT NO. : 6,733,539 B2
DATED : May 11, 2004
INVENTOR(S) : Grégory Plos

It is certified that error appears in the above-identified patent and that said Letters Patent is hereby corrected as shown below:

<u>Column 16,</u>
Line 42, delete "3" after -- β --.

<u>Column 20,</u>
Line 25, "vermicifera" should read -- vernicifera --.

<u>Column 21,</u>
Line 25, "p-hydroxyethyl" should read -- β-hydroxyethyl --.

Signed and Sealed this

Fifteenth Day of February, 2005

JON W. DUDAS
*Director of the United States Patent and Trademark Office*